US006531155B1

(12) United States Patent
Schade et al.

(10) Patent No.: US 6,531,155 B1
(45) Date of Patent: Mar. 11, 2003

(54) GRANULATES FOR COSMETIC AND PHARMACEUTICAL PREPARATIONS

(75) Inventors: Christian Schade, Ludwigshafen (DE); Robert Heinz, Ludwigshafen (DE); Thekla Börs, München (DE); Hans-Ulrich Wekel, Ellerstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 906 days.

(21) Appl. No.: 09/101,234

(22) PCT Filed: Jan. 3, 1997

(86) PCT No.: PCT/EP97/00014

§ 371 (c)(1),
(2), (4) Date: Jul. 6, 1998

(87) PCT Pub. No.: WO97/25027

PCT Pub. Date: Jul. 17, 1997

(30) Foreign Application Priority Data

Jan. 8, 1996  (DE) .......................................... 196 00 324

(51) Int. Cl.⁷ ................................................. A61K 9/14
(52) U.S. Cl. ....................... 424/489; 424/474; 424/475; 424/479; 424/481; 424/482; 424/486; 424/487; 424/500; 424/501; 424/502
(58) Field of Search ................... 424/474, 475, 424/476, 479, 481, 482, 486, 487, 489, 500, 501, 502

(56) References Cited

U.S. PATENT DOCUMENTS

| | | | |
|---|---|---|---|
| 2,798,053 A | 7/1957 | Brown | 260/2.2 |
| 3,459,850 A | 8/1969 | Riva | 424/22 |
| 3,915,921 A | 10/1975 | Schlatzer, Jr. | 260/17 |
| 4,066,583 A | 1/1978 | Spaulding | 260/17 |
| 5,034,486 A | 7/1991 | Tzai et al. | 526/271 |
| 5,034,488 A | 7/1991 | Tazi et al. | 526/271 |
| 5,091,184 A | 2/1992 | Khanna | 424/435 |
| 5,169,645 A | * 12/1992 | Shukla et al. | 424/499 |

FOREIGN PATENT DOCUMENTS

| | | |
|---|---|---|
| DE | 4213283 | 4/1992 |
| DE | 4213971 | 4/1992 |
| DE | 4325158 | 7/1993 |
| EP | 128237 | 12/1984 |
| EP | 238404 | 9/1987 |
| EP | 376891 | 12/1988 |
| EP | 371421 | 6/1990 |
| EP | 436960 | 7/1991 |
| EP | 514008 | 11/1992 |
| EP | 516141 | 12/1992 |
| EP | 584771 | 3/1994 |
| WO | 90/12775 | 11/1990 |
| WO | 92/01724 | 2/1992 |
| WO | 93/23457 | 11/1993 |
| WO | 2167726 | 2/1995 |
| WO | 9503790 | * 2/1995 |

OTHER PUBLICATIONS

*Chem. Ing. Tech.*, vol. 59, No. 10, 1987, 779–787.
*Chemie Technik.*, vol. 4, No. 6, 1975, p. 207–209.
*Aufbereitungs–Technik*, No. 10, 1980, 525–533.
*Eur. I. Pharm. Biopharm.*, 38(6), 1992, 195–198.
*Rheological Prop. of Cosm. and Toil.*, 1993, 55–152.

* cited by examiner

Primary Examiner—Thurman K. Page
Assistant Examiner—Lakshmi Channavajjala
(74) Attorney, Agent, or Firm—Keil & Weinkauf

(57) ABSTRACT

Granular materials are obtainable by pressing mixtures of at least one pulverulent, rheology-modifying, carboxyl-containing polymer as main component and at least one oil-soluble component.

10 Claims, No Drawings

GRANULATES FOR COSMETIC AND PHARMACEUTICAL PREPARATIONS

The present invention relates to granular materials obtainable by pressing mixtures of at least one pulverulent, rheology-modifying, carboxyl-containing polymer as main component and at least one oil-soluble component.

It is known that weakly crosslinked polycarboxylic acids, which may be hydrophobicized, are widely used in cosmetics, medicine and pharmacy. Such polymers are marketed, for example, under the trade names Carbopol®, Pemulen®, Synthalen®, Rheolate®, Stabylen®, Acrisint®, Junlon®, Hypan® or Hivis®.

These products are finely divided, often easily electrostatically chargeable and very dusty powders. The high proportion of fines in these powders leads to a series of disadvantages in processing, for example ready demixing of the variously sized particles, agglomerate formation, unfavorable flow behavior and material losses resulting from a fine dust. In addition, this fine dust causes health hazards, since an appreciable proportion of this dust has a particle diameter of less than 5 $\mu$m and is therefore able to get into the lungs. The processing of these polymers therefore requires special safety and occupational hygiene measures.

Press agglomeration enables the particle size of polymers to be increased and thus the handleability of the powders to be improved. In Chem. Ing.-Tech. 59 (1987) No. 10: 779–787, Chemie-Technik, Vol. 4, (1975) No. 6: 207–209, and Aufbereitungs-Technik (1980) No. 10: 525–533, the principles of press agglomeration are described for the example of fertilizers. For good press agglomeration, low moisture contents of the material to be pressed are advantageous. For the compaction it is typical that neither moisture nor binder are added during the process. The binder-free press agglomeration allows exclusively binding mechanisms within the polymer to become effective under high pressures.

If the material to be granulated does not have the necessary binding properties under the pressure of the granulating tools, solid or liquid components can be added in exceptional cases to improve the binding.

The press agglomeration of polymers is described, for example, in Eur. J. Pharm. Biopharm 38 (1992), No. 6, 195–198 or in WO 93/23457. These products are suitable for the production of aqueous gels, but are unsuitable for the production of oil-containing systems since they form lumps of gel. In the production of oil-containing systems such as emulsions, it is customary first to disperse the polymers in the oil phase and subsequently to add further components such as water and/or a base. The pressed agglomerates produced according to the prior art do not disintegrate completely in the oil phase under the given conditions, so that the subsequent addition of water and/or a base results in the formation of mixtures containing large, lumpy pieces of gel which undergo strong further swelling: these mixtures are not usable in cosmetics and pharmaceuticals.

It is an object of the present invention to develop low-dust, free-flowing granular materials comprising pulverulent polymer which can be incorporated into oil phases without the disadvantages described and make them available for applications in the cosmetic and pharmaceutical sector.

We have found that this object is achieved by addition of at least one oil-soluble component to the pulverulent polymer before or during press agglomeration to give a granular material which can be dispersed very well in oil and additionally can be handled without complicated safety measures.

The granular materials of the present invention dissolve without formation of lumps of gel and thus form homogeneous emulsions. They are therefore very well suited to the production of pharmaceutical and in particular cosmetic preparations based on oil-in-water emulsions. The present invention accordingly provides for the use of the above-described granular materials and corresponding preparations.

Granulatable carboxyl-containing polymers are commercially available or described in the literature. For example, a listing of products commercially used in cosmetics may be found in D. Laba (Editor), Rheological Properties of Cosmetics and Toiletries, M. Dekker Inc., 1993, pages 55 to 152. Preference is given to using polycarboxylic acids and polycarboxylic acid copolymers.

These weakly crosslinked polycarboxylic acids, which may be hydrophobicized, are preferably prepared by precipitation polymerization in organic media. DE-A-43 25 158 describes the precipitation polymerization methods. Examples of such polymers are given in the patents EP-A-128 237, EP-A-584 771, EP-A-371 421, EP-A-470 098, U.S. Pat. Nos. 4,066,583, 3,915,921, 2,798,053, 5,034,486, 5,034,488, WO 92/01724, EP-A-238 404, EP-A-436 960, DE-A-4 213 283, DE-A-4 213 971 or DE-A-4 325 158.

According to the present invention, it is particularly advantageous to granulate pulverulent, rheology-modifying, carboxyl-containing polymers obtainable by free-radical-initiated copolymerization of monomer mixtures comprising a) 40–99.99% by weight of a monoethylenically unsaturated $C_3$–$C_6$-monocarboxylic acid, a monoethylenically unsaturated $C_4$–$C_8$-dicarboxylic acid or their anhydrides or salts or mixtures of the specified carboxylic acids, their anhydrides and/or salts, b) 0.01–10% by weight of a crosslinker, c) 0–20% by weight of an ester of a monoethylenically unsaturated $C_3$–$C_8$-monocarboxylic or dicarboxylic acid with at least one linear or branched $C_1$–$C_{40}$-alcohol, and d) 0 to 60% by weight of other monomers copolymerizable with the monomers (a), (b) and (c), where the various monomers add up 100%.

The monomers a) are monoethylenically unsaturated $C_3$–$C_8$-monocarboxylic and dicarboxylic acids, their anhydrides, their salts or mixtures of the specified carboxylic acids, anhydrides and salts. Suitable carboxylic acids are, for example, acrylic acid, methacrylic acid, maleic acid, fumaric acid, itaconic acid or crotonic acid. Suitable anhydrides are, for example, acrylic anhydride, methacrylic anhydride or maleic anhydride. Among the monomers of the group a) preference is given to using acrylic acid, methacrylic acid, maleic acid and/or maleic anhydride. The monomers can be present in the monomer mixtures to be polymerized in amounts of, for example, 40–99.99% by weight. If the monomer a) is fumaric acid, maleic acid or maleic anhydride, it is particularly preferably used in amounts of 50–80%, very particularly preferably in amounts of 50–64.8% by weight. If the monomer a) is acrylic or methacrylic acid, it is particularly preferably used in amounts of 70–99.93%, very particularly preferably in amounts of 85–99.8% by weight.

The monomers a) can also be partly incorporated in the form of their salts. This can be achieved, for example, by addition of at least one base before, during or after the polymerization. If the polymers are used in the form of their salts, up to 90 mol %, preferably up to 40 mol %, of the carboxyl functions have been converted. However, in the particularly preferred case, over 90 mol % of the carboxyl groups are present in free form or as anhydride.

If the monomers are present in the form their salts, preference is given to the alkaline earth metal, alkali metal or ammonium salts or the salts of organic amines; particularly preference is given to the alkali metal or ammonium salts.

Crosslinkers used for this purpose are generally known compounds, in particular monomers containing at least 2 monoethylenically unsaturated groups in the molecule.

Suitable crosslinkers of this type are, for example, acrylic esters, methacrylic esters, allyl ethers or vinyl ethers of at least dihydric alcohols. The OH groups of the parent alcohols can here be completely or partially etherified or esterified. Examples of dihydric alcohols which can be used are 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, neopentyl glycol hydroxypivalate, 2,2-bis(4-hydroxyphenyl) propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and also polyethylene glycols, polypropylene glycols and polytetrahydrofurans having mean molecular weights of from 200 to 10000 in each case. Apart from the homopolymers of ethylene oxide or propylene oxide, it is also possible to use block copolymers of ethylene oxide or propylene oxide or copolymers incorporating ethylene oxide and propylene oxide groups. Examples of parent alcohols having more than two OH groups are trimethylolpropane, glycerol, pentaerythritol, 1,2,5-pentanetriol, 1,2,6-hexanetriol, triethoxycyanuric acid, sorbitan, sugars such as sucrose, glucose and mannose. Of course it is also possible to use the polyhydric alcohols after reaction with ethylene oxide or propylene oxide as the corresponding ethoxylates or propoxylates.

Further suitable crosslinkers are the vinyl esters or the esters of monohydric, unsaturated alcohols with ethylenically unsaturated $C_3$–$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamic alcohol, citronellol, crotyl alcohol or cis-9-octadecen-1-ol. However, it is also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers are esters of unsaturated carboxylic acids with the above-described polyhydric alcohols, for example oleic acid, crotonic acid, cinnamic acid or 10-undecenoic acid.

Also suitable are straight-chain or branched, linear or cyclic, aliphatic or aromatic hydrocarbons having at least two double bonds which in the case of aliphatic hydrocarbons must not be conjugated, eg. divinylbenzene, divinyltoluene, 1,7-octadiene, 1,9-decadiene, 4-vinyl-1-cyclohexene, trivinylcyclohexane or polybutadienes having mean molecular weights of 200–20000. Also suitable as crosslinkers are acrylamides and methacrylamides of at least difunctional amines, so that the amides contain at least two double bonds. Examples of such amines are diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids such as acrylic acid, methacrylic acid, itaconic acid, maleic acid, or at least dibasic carboxylic acids as described above.

Also suitable are N-allyl or N-vinyl compounds of urea derivatives, at least difunctional amides, cyanurates or urethanes, for example of urea, ethyleneurea, propyleneurea or tartaric diamide.

Further suitable crosslinkers are divinyldioxane, diallyl phosphate, triallyl phosphate, triallyltriazinetrione, diallylamine, triallylamine, tetraallylsilane, tetravinylsilane, hexaallyl(trimethylene trisulfone), butadiene or isoprene. It is naturally also possible to use mixtures of the abovementioned compounds.

Preference is given to using (meth)acrylic esters of $C_2$–$C_6$-diols, allyl ethers of polyhydric alcohols such as trimethylolpropane, pentaerythritol, sucrose or sorbitol, which ethers have more than one allyl ether function in the molecule, (meth)acrylic esters of unsaturated $C_3$–$C_{24}$-alcohols, eg. oleyl (meth)acrylate, trivinylcyclohexane and/or non-conjugated $C_6$–$C_{16}$-alkadienes and also divinyl glycol. Very particular preference is given to using allyl ethers of pentaerythritol or sucrose having more than two ally ether functions in the molecule, allyl (meth)acrylate, (meth) acrylic esters of unsaturated $C_{12}$–$C_{20}$-alcohols, trivinylcyclohexane and/or non-conjugated $C_8$–$C_{14}$-alkadienes. If crosslinking monomers b) are present, they can be used in amounts of from 0.01 to 10% by weight. Preference is given to using from 0.05 to 5% by weight, particularly preferably from 0.1 to 3% by weight, of the monomers b).

Monomers of the group c) are acrylic esters or methacrylic esters of saturated, linear or branched $C_1$–$C_{40}$-alcohols. Examples are methyl, ethyl, n-propyl, i-propyl, n-butyl, i-butyl, tert-butyl, n-hexyl, n-octyl, i-nonyl, n-decyl, n-dodecyl, n-tetradecyl, n-hexadecyl, n-heptadecyl, n-octadecyl, n-nonadecyl, n-eicosyl, n-docosyl, n-tetracosyl, 2-ethylhexyl, i-bornyl and cyclohexyl acrylates, and the corresponding methacrylates. Preference is given to using $C_1$-, $C_2$- and/or $C_6$–$C_{30}$-alkyl acrylates or methacrylates. Particular preference is given to using $C_8$–$C_{22}$-alkyl acrylates or methacrylates. It is naturally also possible to use mixtures of the monomers c). The monomers c) are, if they are used, present in amounts of up to 20% by weight, preferably from 0.02 to 10% by weight, very particularly preferably from 0.1 to 5% by weight.

Further monoethylenically unsaturated monomers d) can be present in the monomer mixture. Preferred monomers are, for example, N-vinyl compounds such as N-vinylpyrrolidone, N-vinylimidazole, N-vinylcaprolactam, 1-vinyl-3-alkylimidazolium salts having from 8 to 30 carbon atoms in the alkyl chain, acrylamide, methacrylamide, N-($C_1$–$C_{18}$-alkyl)acrylamides or N-($C_1$–$C_{18}$) methacrylamides, eg. N,N-dimethylacrylamide, N-tert-butylacrylamide, N-tert-octylacrylamide, N-dodecylacrylamide, N-methylundecylacrylamide or N-stearylacrylamide, vinyl esters of saturated $C_1$–$C_{30}$-carboxylic acids such as vinyl acetate, vinyl propionate, vinylneononanoate, vinylneodecanoate or vinyllaurate, hydroxyalkylene mono(meth)acrylates having from 2 to 6 carbon atoms in the alkylene group, (meth)acrylic esters of $C_1$–$C_{30}$-alcohols reacted with from 2 to 50 ethylene oxide units, $C_1$–$C_{30}$-alkyl vinyl ethers, straight-chain or branched, linear or cyclic $C_4$–$C_{40}$-alkenes having a terminal double bond, for example Isobutene, diisobutene, 1-tetracosene, 1-docosene 1-eicosene 1-octadecene, 1-heptadecene, 1-hexadecene, 1-tetradecene, 1-dodecene, 1-decene, cyclododecene, cyclooctene, styrene, α-methylstyrene, acrylonitrile, methyl vinyl ketone, vinyl chloride, vinylidene chloride or mixtures of these. Particular preference is given to acrylamide, N-vinylpyrrolidone, vinyl acetate, vinyl methyl ether, vinyl ethyl ether or $C_4$–$C_{30}$-alkenes. Very particular preference is given to vinyl methyl ether or $C_{14}$–$C_{22}$-alkenes. If the monomers are present, they are used in an amount of up to 60% by weight. In a first preferred range, use is made of up to 10% by weight, in particular up to 5% by weight, of the monomers d), when a) is acrylic or methacrylic acid. In a further preferred range, the monomer d) is used in amounts of from 20 to 60% by weight, particularly preferably from 35 to 50% by weight, when a) is fumaric acid, maleic acid or maleic anhydride. The preferred monomer d) is then vinyl methyl ether, vinyl ethyl ether, isobutene or diisobutene, very particularly preferably vinyl methyl ether, while the monomer a) used is then frequently essentially maleic anhydride. In all cases it is naturally also possible to use mixtures of the monomers d).

In the preparation of the polymers from the monomers a) to d), additives which can influence the polymerization process or the properties of the polymer powder may also be present. Such additives are, in particular protective colloids or emulsifiers. Preferred emulsifiers are often nonionic, low molecular weight or polymeric, random or block-type compounds. Such additives may sometimes also be incorporated as a constituent of the polymer, as described, for example, in EP-A-584 771 and the documents cited therein. If such additives are present, they are used in amounts of up to 20% by weight, preferably up to 10% by weight, based on the polymer weight.

The polymers described can also be prepared in the presence of sugars, sugar derivatives and/or proteins. Examples of sugar and/or sugar derivatives are glucose, sucrose, mannose, starch hydrolysates, starch, cellulose or cellulose ethers. The proportion of these compounds can be up to 80% by weight, preferably up to 50% by weight, based on the weight of the monomer mixture of a) to d)).

The polycarboxylic acid copolymers advantageously used for the formation of the granular material can be prepared by various methods such as precipitation polymerization, reverse emulsion polymerization, reverse suspension polymerization, emulsion polymerization or solution polymerization. They are, possibly after further process steps such as spray drying, in the form of finely divided powders. At least 10% by weight of the particles of the finely divided polymer powder should preferably have a particle diameter of below 300 μm. Preference is given to using dusty powders in which over 30% by weight of the particles have a diameter of below 100 μm.

The polymer powders described are processed in the presence of at least one oil-soluble component to give low-dust granular materials.

Suitable oil-soluble components are many polymers which preferably have an oily or wax-like consistency. Examples are fully or partially hydrogenated polybutadienes, polyisoprenes or their copolymers with styrene, polyolefin homopolymers and copolymers having a mean molecular weight of less than 20,000 or copolymers of N-vinylpyrrolidone with $C_4$–$C_{40}$-alkenes.

Also suitable are silicones, in particularly silicone oils, which can have a linear, branched or cyclic structure. A preferred class of substances comprises the materials known as cyclomethicones.

Other oil-soluble components which can be employed are solvents insoluble or sparingly soluble in water and having a boiling point of above 150° C., for example dialkyl phthalates having from 4 to 12 carbon atoms in the alkyl radical.

Examples of the oil-soluble group also include waxes, for example plant waxes such as carnauba wax, candelilla wax, ouricurry wax, sugar cane wax, retamo wax, animal waxes such as beeswax, shellac waxes, insect waxes or wool waxes, petroleum, rayon coal, peat and other montan waxes, polyolefin waxes, paraffin waxes, acid waxes, ester waxes, alcohol or amide waxes. The waxes can be in a natural state, modified, partially synthetic or fully synthetic. It is of course also possible to use individual wax components such as wax acids, wax alcohols, wax ketones, hydroxy-wax acid, paraffins, resin acids, polyterpenes, resin alcohols, stearins or fatty acids or mixtures thereof.

Further suitable oil-soluble components are nonionic emulsifiers. Commercial emulsifiers are cited, for example, in M. and I. Ash, Handbook of Industrial Surfactants, Gower Publishing Co., Hants, 1993. They can be low molecular weight or polymeric compounds. Low molecular weight compounds generally contain a straight-chain or branched, saturated or unsaturated, cyclic or acyclic, aromatic or aliphatic alkyl [sic] radical having from 8 to 40, preferably from 10 to 30, very particularly preferably from 12 to 22, carbon atoms in the molecule. The alkyl [sic] radical can also be fully or partially fluorinated. The alkyl [sic] radical is bound to a hydrophilic section of the molecule which contains at least the one oxygen or nitrogen atom.

Also suitable are sterols such as cholesterol or terpenoids such as vitamin E.

Preference is given to using oils or fats as oil-soluble component. Examples of these are paraffin oils, vaseline, saturated or unsaturated, straight-chain or branched $C_6$–$C_{30}$-fatty acids, such as ethylhexanoic acid, myristic acid, capric acid, lauric acid, stearic acid, palmitic acid, isostearic acid, eicosanoic acid, docosanoic acid, tetracosanoic acid, oleic acid, linoleic acid, linolenic acid, nervonic acid, α-hydroxynervonic acid, elaidic acid, ricinoleic acid, erucic acid, margaric acid, palmitoleic acid, stearolic acid, $C_6$–$C_{30}$-fatty esters or benzoic esters of $C_1$–$C_{30}$-alcoholes such as methanol, ethanol, iso-propanol, propanol, butanol, hexanol, octanol, decanol, dodecanol, tetradecanol, hexadecanol, octadecanol, 2-ethyl-1-hexanol, eicosanol, docosanol, tetracosanol, pentaerythritol, glycerol, diglycerol or polyglycerol, natural oils and fats of plant or animal origin such as train oils, peanut oil, rape seed oil, coconut oil, palm kernel oil, palm oil, rape oil, olive oil, linseed oil, cottonseed oil, thistle oil, maize oil, sunflower oil, sesame oil, avocado oil, soybean oil, mustard oil, almond oil, cocoa butter, castor oil, jojoba oil, fish oils, tallow oil, fats or tallow from cattle, pigs or sheep, $C_6$–$C_{30}$-alcohols or products obtained therefrom by ethoxylation, or silicone oils.

The oil-soluble component has a room-temperature solubility of at least 2% by weight in paraffin oil, silicon oil or isopropyl myristate.

Particular preference is given to using oils which are also used in cosmetic or pharmaceutical formulations. Such oils are described, for example, in M. and I. Ash, Handbook of Cosmetic and Personal Care Additives, Gower Publishing Co., Aldershot, 1994 or in H. Fiedler, Lexikon oder [sic] Hilfsstoffe, editio cantor, Aulendorf, 1989.

Very particular preference is given to using castor oil, almond oil, paraffin oil, Finsolv®TN ($C_{12}$–$C_{15}$-alkyl benzoate), Luvitol®EHO (cetyl/stearyl ester of 2-ethylhexanoic acid), Witconol® (3-myristyl ether of PPG), Miglyol®812 (caprylic/capric triglyceride), Miglyol®840 (propylene glycol diester of caprylic/capric acid), Crodamol®ISNP (isostearyl neopentanoate), diisopropyl adipate, isopropyl myristate, Eutanol®G (2-octyldodecanol), Cetiol®A (hexyl laurate), Cetiol®HE (PEG-7-glyceryl ester of coconut oil), Cetiol®LC (caprylic/caproic ester of saturated $C_{12-18}$-fatty alcohols), Cetiol®SN (cetyl/stearyl isononanoate), Cetiol®V (decyl oleate), Amerchol®L-101 (lanolyl alcohol and mineral oil) or Dow Corning®344 (cyclomethicone).

Paraffin oil is most frequently used.

The oil-soluble components are added in amounts of from 0.1 to 100% by weight, preferably from 1 to 50% by weight, very particularly preferably from 2.5 to 30% by weight, based on the weight of the polymer powder used.

The polymer powders described are processed in the presence of the oil-soluble component(s) by means of press agglomeration to give low-dust granular materials. Particularly suitable methods are: compaction using roller presses, with subsequent comminution, fractionation and return, but also agglomeration on other presses, eg. by tabletting.

Compaction can be carried out by feeding the polymer powder by means of a feed screw into the gap between two contrarotating rollers and pressing it between the rollers at pressures of generally from 10 MPa to 300 MPa, preferably 20–100 MPa. The resulting band is broken up in a disintegrator and, for example by means of a screen disintegrator, kept to the desired size.

From the resulting broad agglomerate distribution, the material whose particle size is smaller than the desired lower limit is subsequently separated off by means of a screen or sifter and is returned to the compacting apparatus together with further powder to be compacted.

The low-dust granular materials obtained by press agglomeration preferably have mean particle sizes in the range 20 μm–10 mm, preferably 100 μm–5 mm, very particularly preferably from 0.5 to 3 mm.

The granular materials thus produced dissolve particularly readily in oil and are suitable for the production of pharmaceutical and, in particular, cosmetic preparations based on oil-in-water emulsions.

For the purposes of the present invention, pharmaceutical preparations are, for example, gels, pastes, creams, lotions, emulsions and ointments for use on healthy, diseased or injured skin or mucus membranes, without being restricted to these preparations or fields of use.

A particularly interesting possible application of the granular materials is the production of transdermal therapeutic systems.

For the purpose of the present invention, cosmetic preparations are, for example, skin care products, washing and cleaning compositions for skin, hair and body care compositions, hair styling compositions, dental care compositions, eye care compositions, foot care compositions, repellants and sun protection compositions in the form of gels, creams, lotions, emulsions, foams and balsams, without being restricted to these preparations or uses.

EXAMPLES

Granulation of Carboxyl-containing Polymers

Polymer 1: Copolymer of acrylic acid, stearyl methacrylate and oleyl methacrylate in a weight ratio of 98/1/1, prepared by precipitation polymerization in cyclohexane Polymer 2: Crosslinked copolymer of acrylic acid (about 97% by weight) and stearyl methacrylate (about 2.5% by weight), prepared by precipitation copolymerization in mixtures of ethyl acetate and cyclohexane, sold by B. F. Goodrich under the name Permulen® TR 1

Polymer 3: Copolymer of methacrylic acid, ethyl acrylate and a methacrylic ester of a $C_{16}/C_{18}$-fatty alcohol reacted with 15 ethylene oxide units, the monomers being in a weight ratio of 60/83/8, prepared by emulsion polymerization in water and subsequent spray drying.

Oil 1: Fluid paraffin oil in accordance with Pharmakopöe Helvetika

Oil 2: Paraffin oil having a viscosity (20° C.) of 110 mPas

Oil 3: Isopropyl myristate

Oil 4: Sunflower oil

Example 1

Polymer 1 was processed in a compacting unit to give a low-dust granular material. For this purpose, the powder was first mixed with 20% by weight of oil 1 and subsequently fed from a funnel by means of a feed screw into the gap of a pair of rollers (roller diameter=200 mm, roller width=50 mm) and pressed between the rollers at pressures of about 80 MPa. The resulting band was subjected to preliminary breaking up using a thread breaker and was restricted to 1.6 mm using a screen disintegrator. The resulting granular material was sieved through a 300 μm screen and the fines were returned to the feed funnel. The useful fraction was a product which was not readily abraded and had a bulk density distinctly higher than that of the starting powder. Despite its strength, the granular material had good dispersibility in oil phases.

Examples 2 to 4

The polymers indicated were mixed with 20% by weight of oil 1 and pressed on a tabletting press at pressures of about 50 MPa. The resulting compacts (diameter=10 mm, height=1.5 mm) were comminuted and classified using a method similar to Example 1.

Example 2: Polymer 1

Example 3: Polymer 2

Example 4: Polymer 3

Examples 5 to 7

Polymer 2 was mixed with 20% by weight of the oil indicated and pressed on a tabletting press at pressures of about 50 MPa. The resulting compacts (diameter=10 mm, height=1.5 mm) were comminuted and classified using a method similar to Example 1.

Example 5: Oil 2

Example 6: Oil 3

Example 7: Oil 4

Examples 8 to 11

Polymer 1 was mixed with different amounts of oil 1 and pressed on a tabletting press at pressures of about 50 MPa. The resulting compacts (diameter=10 mm, height=1.5 mm) were comminuted and classified using a method similar to Example 1.

Example 8: 50% by weight

Example 9: 20% by weight

Example 10: 5% by weight

Example 11: 1% by weight

Processability in Oil 0.4 g of the granular material from Example 1 was added to 30 ml of paraffin oil in a glass beaker and stirred for 1 hour on a magnetic stirrer. After addition of 100 ml of water, stirring was continued for one further hour. Subsequently, 4 ml of a 10% strength triethanolamine solution in water were added and the mixer was stirred with a blade stirrer.

This gave a uniform emulsion which did not change on further standing and had properties corresponding to those of an emulsion which was obtained directly from the uncompacted polymer 1.

Homogenization using an Ultraturrax gave a white, fine emulsion which did not change further even on prolonged standing.

In a similar manner, analogous emulsions were obtained from the granular materials of Examples 2 to 7, with a total of 0.8 g of the granular material being used in Example 4.

The granular materials of Examples 8 to 11 were incorporated into an oil phase using a method similar to Example 1, giving similarly good results to Example 1. However, Example 11 required about double the dispersion time in the paraffin oil in order to obtain an emulsion free of gel particles.

Comparative Example

In a similar manner to Example 1, a granular material was produced from polymer 1 without addition of the paraffin oil 1. The product was processed to give an emulsion in a similar manner to that described above. After stirring for one hour with the magnetic stirrer, the granules had not yet disintegrated or had only disintegrated very incompletely. Addition of the water phase resulted in relatively large lumps of gel which did not dissolve. Even after addition of base and intensive stirring with the blade stirrer, large lumps of gel remained. Even considerable prolonging of the stirring-in and dispersion times brought no significant change. Homogenization gave an initially white emulsion in which, however, clear, swollen lumps of gel were present.

We claim:

1. A granular material obtainable by pressing mixtures of at least one carboxyl-containing polymer as main component and at least one oil-soluble component, wherein use is made of a polymer component obtainable by free-radical-initiated copolymerization of monomer mixtures comprising
    a) from 50 to 99.93% by weight of a monoethylenically unsaturated $C_3$–$C_6$-monocarboxylic acid, a monoethylenically unsaturated $C_4$–$C_8$-dicarboxylic acid or their anhydrides or salts or mixtures of the specified carboxylic acids, their anhydrides and/or salts,
    b) from 0.05 to 5% by weight of one or more compounds having at least two ethylenically unsaturated, nonconjugated double bonds in the molecule as crosslinker,
    c) from 0.02 to 10% by weight of at least one $C_1$–$C_{30}$-alkyl (meth)acrylate and
    d) from 0 to 50% by weight of other water-insoluble monomers copolymerizable with the monomers (a), (b) and (c).

2. A granular material as claimed in claim 1, wherein use is made of a polymer component obtainable by free-radical-initiated copolymerization of monomer mixtures comprising
    a) from 85 to 99.8% by weight of acrylic acid or methacrylic acid or from 50 to 64.8% by weight of fumaric acid, maleic acid or maleic anhydride,
    b) from 0.1 to 3% by weight of at least one allyl ether of polyhydric alcohols having more than one allyl ether function in the molecule or esters of monoethylenically unsaturated carboxylic acids with $C_3$–$C_{24}$-alcohols, trivinylcyclohexane or divinyl glycol,
    c) from 0.1 to 5% by weight of at least one $C_8$–$C_{24}$-alkyl (meth)acrylate and
    d) 0–5% by weight (in the case of acrylic acid or methacrylic acid as monomer component (a)) or 35–50% by weight (in the case of fumaric acid, maleic acid or maleic anhydride) of other $C_4$–$C_{30}$-alkenes copolymerizable with the monomers (a), (b) and (c).

3. A granular material as claimed in claim 1 obtainable by pressing the polymer powders with waxes, nonionic emulsifiers, fats and/or oils.

4. A granular material as claimed in claim 1 obtainable by pressing the polymer powders with oils customary in cosmetics and/or pharmacy.

5. A granular material as claimed in claim 1 obtainable by pressing the polymer powders with from 0.1 to 100% by weight of the oil-soluble component, based on the polymer weight.

6. A granular material as claimed in claim 1 obtainable by pressing the polymer powders with from 1 to 50% by weight of the oil-soluble component, based on the polymer weight.

7. A granular material as claimed in claim 1 obtainable by pressing the polymer powders with from 2.5 to 30% by weight of the oil-soluble component, based on the polymer weight.

8. A granular material as claimed in claim 1 having a mean particle size in the range from 20 μm to 10 mm.

9. A process for producing a granular material as claimed in claim 1, which comprises pressing the carboxyl-containing polymer powders in the presence of at least one oil-soluble component.

10. A cosmetic or pharmaceutical preparation comprising a granular material as claimed in claim 1 customary additives.

* * * * *